US010109045B2

(12) United States Patent
Kobayashi et al.

(10) Patent No.: US 10,109,045 B2
(45) Date of Patent: Oct. 23, 2018

(54) DEFECT INSPECTION APPARATUS FOR INSPECTING SHEET-LIKE INSPECTION OBJECT, COMPUTER-IMPLEMENTED METHOD FOR INSPECTING SHEET-LIKE INSPECTION OBJECT, AND DEFECT INSPECTION SYSTEM FOR INSPECTING SHEET-LIKE INSPECTION OBJECT

(71) Applicants: Hiroaki Kobayashi, Tokyo (JP); Makoto Hino, Kanagawa (JP); Keiichi Miyamoto, Kanagawa (JP)

(72) Inventors: Hiroaki Kobayashi, Tokyo (JP); Makoto Hino, Kanagawa (JP); Keiichi Miyamoto, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 118 days.

(21) Appl. No.: 15/202,921

(22) Filed: Jul. 6, 2016

(65) Prior Publication Data

US 2017/0011502 A1 Jan. 12, 2017

(30) Foreign Application Priority Data

Jul. 10, 2015 (JP) ................................ 2015-139165
Mar. 10, 2016 (JP) ................................ 2016-047457

(51) Int. Cl.
*G06K 9/00* (2006.01)
*G06T 7/00* (2017.01)
*G06T 7/41* (2017.01)

(52) U.S. Cl.
CPC .............. *G06T 7/0004* (2013.01); *G06T 7/41* (2017.01); *G06T 2207/20021* (2013.01); *G06T 2207/30124* (2013.01)

(58) Field of Classification Search
None
See application file for complete search history.

(56) References Cited

U.S. PATENT DOCUMENTS 5,748,300 A * 5/1998 Wilder ............... G01M 11/0214 356/124
2004/0076739 A1* 4/2004 Yokono ................. G01N 21/88 427/8

(Continued)

FOREIGN PATENT DOCUMENTS

JP H06-207909 7/1994
JP 08145907 * 11/1994 ........... G06T 7/0004
JP H08-145907 6/1996

*Primary Examiner* — Sean Conner
(74) *Attorney, Agent, or Firm* — Duft Bornsen & Fettig LLP

(57) ABSTRACT

An apparatus divides a photographed image of a sheet-like inspection object into blocks each of which has a size of a predetermined number of pixels by a predetermined number of pixels, calculates a longitudinal variance based on pixel values in a longitudinal direction in each block and a lateral variance based on pixel values in a lateral direction in the block, determines whether the block is a defect candidate using the longitudinal variance and the lateral variance as sheet-like inspection object defect determination evaluation values, and determines, based on one of a length and an area of the blocks determined as the defect candidates, whether the sheet-like inspection object has defect.

17 Claims, 10 Drawing Sheets

(56) References Cited

U.S. PATENT DOCUMENTS

| | | | | |
|---|---|---|---|---|
| 2007/0179663 | A1* | 8/2007 | McIntyre | G05B 23/0229 700/210 |
| 2008/0205747 | A1* | 8/2008 | Kuchii | G06T 5/20 382/149 |
| 2012/0121139 | A1* | 5/2012 | Kojima | B41F 33/0036 382/112 |

* cited by examiner

FIG.6A

| | 1 | 2 | 3 | 4 | 5 | 6 | 7 | 8 | 9 | 10 | | AVERAGE | AVERAGE OF AVERAGES | SECOND POWER OF AVERAGE |
|---|---|---|---|---|---|---|---|---|---|---|---|---|---|---|
| 1 | 135 | 139 | 145 | 131 | 132 | 133 | 134 | 135 | 136 | 137 | | 135.7 | 131.3 | 18414 |
| 2 | 128 | 129 | 130 | 135 | 139 | 145 | 134 | 135 | 136 | 137 | | 134.8 | | 18171 |
| 3 | 128 | 129 | 130 | 131 | 132 | 133 | 134 | 135 | 136 | 137 | | 132.5 | | 17556 |
| 4 | 128 | 129 | 130 | 131 | 132 | 135 | 139 | 145 | 136 | 137 | | 134.2 | | 18010 |
| 5 | 128 | 125 | 132 | 132 | 134 | 125 | 138 | 125 | 142 | 134 | | 131.5 | | 17292 |
| 6 | 128 | 125 | 132 | 132 | 134 | 112 | 120 | 125 | 142 | 134 | | 128.4 | | 16487 |
| 7 | 128 | 125 | 132 | 132 | 120 | 125 | 138 | 125 | 142 | 121 | | 128.8 | | 16589 |
| 8 | 128 | 125 | 132 | 115 | 120 | 125 | 138 | 120 | 142 | 134 | | 127.9 | | 16358 |
| 9 | 128 | 125 | 132 | 132 | 134 | 125 | 138 | 125 | 121 | 134 | | 129.4 | | 16744 |
| 10 | 128 | 125 | 132 | 132 | 120 | 125 | 138 | 125 | 142 | 134 | | 130.1 | | 16926 |
| | | | | | | | | | | | SUM OF AVERAGES | 1313.3 | SUM OF SECOND POWERS OF AVERAGES | 172547 |
| AVERAGE | 128.7 | 127.6 | 132.7 | 130.3 | 129.7 | 128.3 | 135.1 | 129.5 | 137.5 | 133.9 | | | LATERAL VARIANCE | 7.1311 |
| SUM OF AVERAGES | 1313.3 | | | | | | | | | | | | | |
| AVERAGE OF AVERAGES | 131.3 | | | | | | | | | | | | | |
| SECOND POWER OF AVERAGE | 16564 | 16282 | 17609 | 16978 | 16822 | 16461 | 18252 | 16770 | 18906 | 17929 | | | | |
| SUM OF SECOND POWERS OF AVERAGES | 172573 | | | | | | | | | | | | | |
| LONGITUDINAL VARIANCE | 9.7311 | | | | | | | | | | | | EVALUATION VALUE | 16.8622 |

FIG.8

| | | |
|---|---|---|
| MAIN SCANNING DIRECTION | 8192 | PIXELS |
| | | |
| [redacted] | | |
| DIRECTIONAL VARIANCES | | |
| 20x20 | | 1580.25 |
| 40x40 | | 888.43 |
| 100x100 | | 320.40 |
| AVERAGING FILTER | | |
| 1x31 | | 314.96 |
| 3x31 | | 148.26 |
| 5x31 | | 95.88 |
| MEDIAN FILTER | | |
| 3x3 | | 169.20 |
| 5x5 | | 36.87 |
| 7x7 | | 5.58 |

DEFECT INSPECTION APPARATUS FOR INSPECTING SHEET-LIKE INSPECTION OBJECT, COMPUTER-IMPLEMENTED METHOD FOR INSPECTING SHEET-LIKE INSPECTION OBJECT, AND DEFECT INSPECTION SYSTEM FOR INSPECTING SHEET-LIKE INSPECTION OBJECT

CROSS-REFERENCE TO APPLICATIONS

The present patent application is based on and claims the benefit of priority of Japanese Priority Application No. 2015-139165, filed on Jul. 10, 2015, and Japanese Priority Application No. 2016-047457, filed on Mar. 10, 2016, the entire contents of which are hereby incorporated herein by reference.

BACKGROUND

1. Technical Field

The present disclosure relates to a defect inspection apparatus for inspecting a sheet-like inspection object, a computer-implemented method for inspecting a sheet-like inspection object, and a defect inspection system for inspecting a sheet-like inspection object.

2. Description of the Related Art

In the related art, a sheet-like inspection object such as a sheet of paper or a plastic (hereinafter, referred to as a "web") is conveyed at high speed, where the sheet-like inspection object is normally wound on a roller, for example. The sheet-like inspection object is then irradiated with light and photographed by a camera, and the sheet-like inspection object is inspected for at least one of a surface shape of the sheet-like inspection object and surface defect such as a stipe, unevenness, and foreign matter.

An apparatus that irradiates a web with illumination light to make a shadow on the web, photographs a regularly reflected image or an irregularly reflected image in the shadow using a camera in a dark field sensitivity region, and carries out image processing on an image signal that represents the photographed image to detect defect is known as one example of a method for inspecting a web to determine whether the web has foreign matter defect.

For example, Japanese Unexamined Patent Application Publication No. H8-145907 discloses an algorithm and a defect inspection apparatus capable of comprehensively determining a type of detected defect, for detecting various types of defect in the defect inspection apparatus.

When the above-mentioned defect inspection apparatus is to detect damage on a web, for example, the defect inspection apparatus uses a longitudinal Sobel filter and a lateral Sobel filter, integrates respective pixel values, and detects defect. When the defect inspection apparatus is to detect unevenness, the defect inspection apparatus divides density information into grids each of which has a pixel matrix of a predetermined number of pixels by a predetermined number of pixels, adds respective pixels of density information together within each grid, acquires lateral and longitudinal density variations between the respective grids, and determines that unevenness occurs if the acquired lateral and longitudinal density variations are greater than predetermined amounts.

The above-mentioned defect inspection apparatus is capable of detecting a plurality of types of defect in the single defect inspection apparatus. However, the defect inspection apparatus uses separate algorithms for detecting respective types of defect such as a stripe, unevenness, and a foreign matter. Therefore, reduction in algorithms concerning program processing (i.e., improvement in the speed of inspecting defect) may be possible, and a lot of inspection processing time may be required.

SUMMARY

According to one aspect, a defect inspection apparatus for inspecting a sheet-like inspection object uses a photographed image of the sheet-like inspection object, the photographed image being input from a photographing apparatus. The defect inspection apparatus includes at least one processor configured to divide the photographed image of the sheet-like inspection object into blocks each of which has a size of a predetermined number of pixels by a predetermined number of pixels, calculate a longitudinal variance based on pixel values in a longitudinal direction in each block and a lateral variance based on pixel values in a lateral direction in the block, determine whether the block is a defect candidate using the longitudinal variance and the lateral variance as sheet-like inspection object defect determination evaluation values, and determine, based on one of a length and an area of the blocks determined as the defect candidates, whether the sheet-like inspection object has defect.

Other objects, features, and advantages will become more apparent from the following detailed description when read in conjunction with the accompanying drawings.

BRIEF DESCRIPTION OF THE DRAWINGS

FIGS. 6A and 6B illustrate an example of calculating a brightness value for each pixel of each block that has the size of 10 pixels by 10 pixels, and calculating directional variances of the blocks;

FIG. 8 illustrates a comparison between a calculation speed for one line to detect web defect using "directional variances", i.e., a longitudinal variance and a lateral variance of brightness, and a process speed for one line using an averaging filter and a median filter.

DETAILED DESCRIPTION OF EMBODIMENTS

An embodiment of the present invention has been devised in consideration of the above-described situation in the related art, and an object of the embodiment of the present invention is to reduce a defect inspection processing time, and achieve improvement in a defect inspection speed.

Below, a defect inspection apparatus and a defect inspection method for inspecting a sheet-like inspection object such as a web according to an embodiment of the present invention will be described with reference to the drawings.

First, a feature of the embodiment of the present invention will be described.

According to the embodiment of the present invention, an image of a web photographed by a camera is divided into a plurality of grid-like blocks, variances of brightness in each block (a longitudinal variance, a lateral variance, and an oblique (for example 45 degrees) variance) of brightness are calculated, a sum total of the calculated variances is compared with criteria (texture brightness), and defect candidate blocks in the web are determined. Next, the determined defect candidate blocks are connected together, and analysis for defect is carried out.

However, calculating the oblique variance may be omitted, and a sum total of the longitudinal variance and the lateral variance may be used instead of the sum total of the longitudinal variance, the lateral variance, and the oblique variance.

Also, instead of a sum total of the calculated variances, it is also possible use the calculated variances themselves to determine defect candidate blocks in the web.

In the analysis for defect, for example, if the connected defect candidate blocks form a line that extends laterally, the blocks may be determined as corresponding to as defect of a lateral stripe. If the defect candidate blocks form a line that extends longitudinally, the blocks may be determined as corresponding to defect of a longitudinal stripe. If the defect candidate blocks are gathered blocks, the blocks may be determined as corresponding to unevenness defect.

Thus, a total sum of variance in each block is used as a target to compare with a criterion to determine whether the block is a defect candidate block. Therefore, because none of a filtering process, an integrating process and an averaging process is carried out, required algorithms can be reduced. And also, because no different algorithms for respective types of defect are used, the required calculation amount can be reduced.

Next, the embodiment of the present invention will be described with reference to the drawings.

Figure 1:
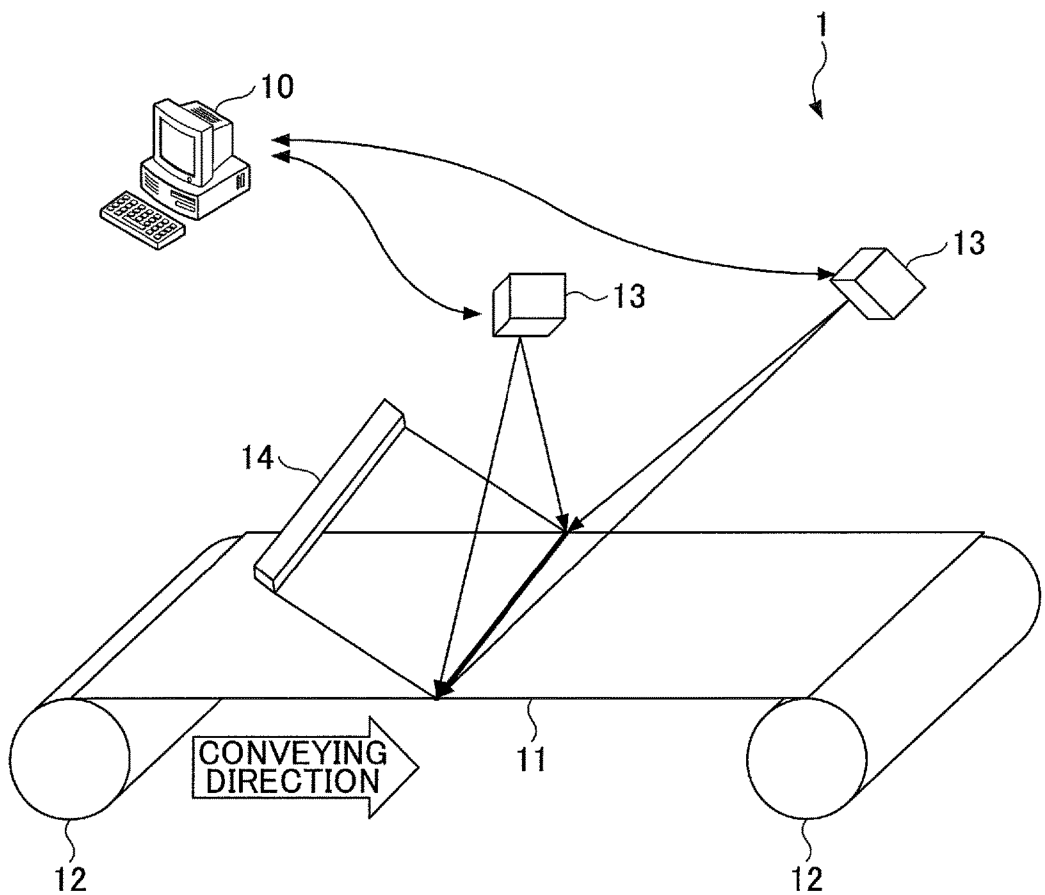
FIG. 1 illustrates an overall perspective view of an inspection system that includes a defect inspection apparatus for inspecting a sheet-like inspection object such as a sheet of paper or a film according to an embodiment of the present invention.

FIG. 1 is a perspective view illustrating the entire configuration of an inspection system 1 that includes a defect inspection apparatus 100 for inspecting a sheet-like member such as a sheet of paper or a film to determine whether the sheet-like member has defect. Note that the inspection system 1 is one example of a defect inspection system. Below, the inspection system 1 will be described as one example of the defect inspection system.

The inspection system 1 includes an inspection personal computer 10, a pair of conveying rollers 12 for conveying a web (a sheet-like inspection object such as a sheet of paper or a film) 11, photographing apparatuses (i.e., line cameras that are one-dimensional CCD cameras) 13 for photographing the web 11, and an illumination apparatus (for example, an LED (light-emitting diode)) 14 for irradiating the web 11. The inspection personal computer 10 inspects the web 11 based on the photographed image of the web 11 to determine whether the web 11 has defect.

The inspection is carried out in such a manner that the LED 14 irradiates the web 11 conveyed by the conveying rollers 12 with illumination light, the line cameras 13 photograph the web 11, image data of the photographed image is input to the inspection personal computer 10, and the image data is inspected.

Note that the inspection personal computer 10 that is one example of the defect inspection apparatus 100 is an information processing apparatus such as a PC (Personal Computer) or a server, and, for example, the inspection personal computer 10 has a hardware configuration that will be described now.

Figure 2:
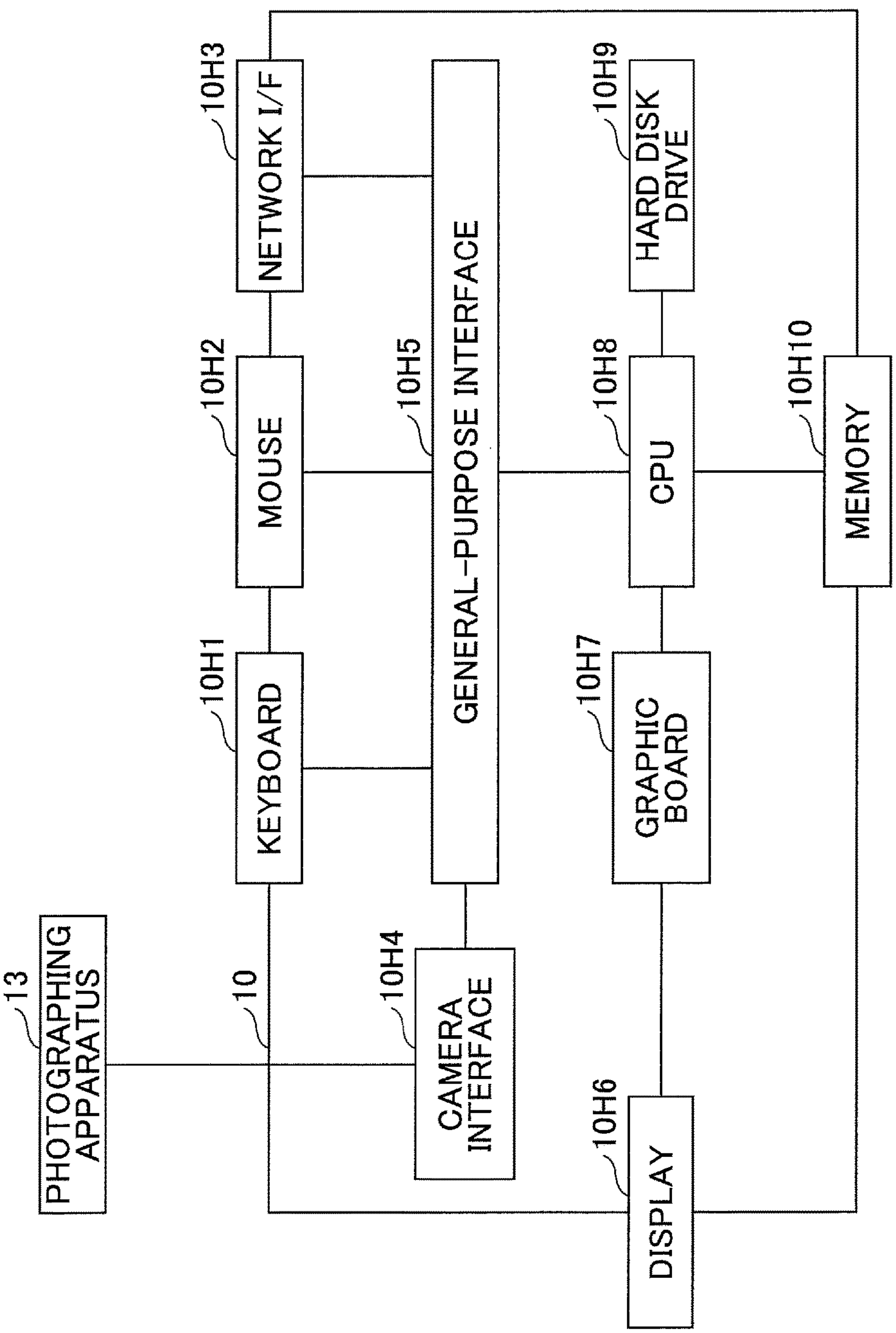
FIG. 2 is a block diagram illustrating one example of a hardware configuration of the defect inspection apparatus illustrated in FIG. 1.

FIG. 2 is a block diagram illustrating one example of a hardware configuration of the defect inspection apparatus 100 illustrated in FIG. 1.

For example, as illustrated in FIG. 2, the inspection personal computer 10 includes inputting devices such as a keyboard 10H1 and a mouse 10H2 for inputting a user's operation. Also, the inspection personal computer 10 has a network interface 10H3 for connecting to a network such as a LAN (Local Area Network). Further, the inspection personal computer 10 has a general-purpose interface 10H5 for connecting peripheral devices such as the keyboard 10H1 and the mouse 10H2, and the network interface 10H3 and the camera interface 10H4 to the inspection personal computer 10. Further, the inspection personal computer 10 has an outputting device such as a display 10H6. The display 10H6 outputs, for example, an image to a user based on an image signal that is input from a graphic board 10H7.

The inspection personal computer 10 further includes a processing device that implements a process such as a CPU (Central Processing Unit) 10H8, and a control device for controlling the hardware. Also, the inspection personal computer 10 has a memory 10H10 to be used as a storage area to be used by, for example, the CPU 10H8 to carry out the process. Note that the memory 10H10 is one example of a main storage. Further, the inspection personal computer 10 includes an auxiliary storage for storing a program and data such as a hard disk drive 10H9.

Thus, the inspection personal computer 10 carries out the process based on the program and so forth. Note that the hardware configuration is not limited to the configuration illustrated in FIG. 2. For example, the inspection personal computer 10 may further include at least one of a processing device, a control device, and a storage. Also, For example, the inspection personal computer 10 may have an electronic circuit such as an ASIC (Application Specific Integrated Circuit) or a FPGA (Field-Programmable Gate Array), and may carry out the process using the electronic circuit.

Figure 3:
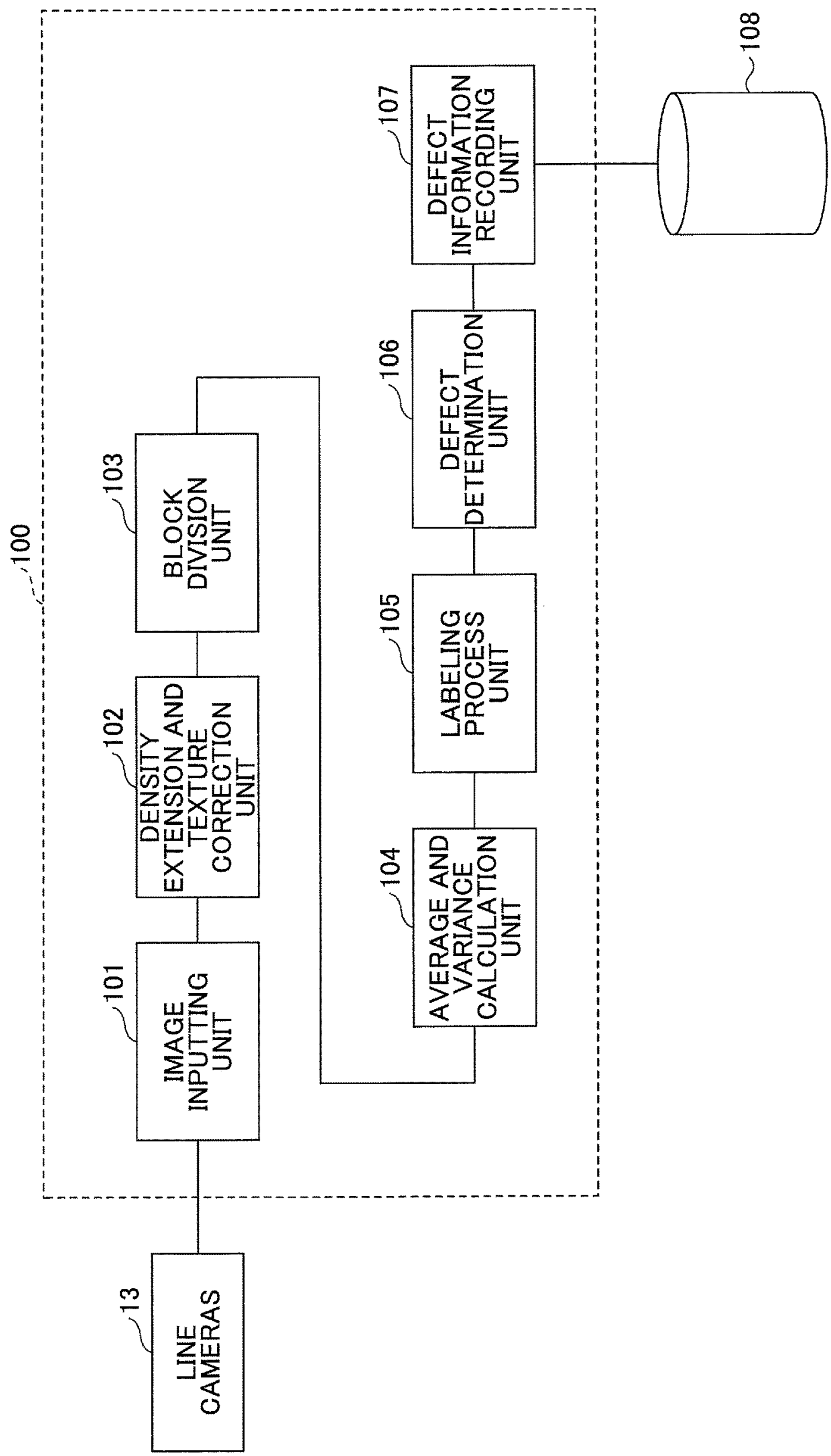
FIG. 3 is a block diagram illustrating a functional block configuration of the defect inspection apparatus illustrated in FIG. 1.

FIG. 3 is a block diagram illustrating a functional block configuration of the defect inspection apparatus 100 illustrated in FIG. 1.

The defect inspection apparatus 100 includes an image inputting unit 101 that inputs image data from the line cameras 13 that are the photographing apparatuses, a density extension and texture correction unit 102 that carries out shading correction on the image data, a block division unit 103 that divides an image represented by the corrected image data, an average and variance calculation unit 104 that calculates a longitudinal variance, a lateral variance, and an oblique variance, a labeling process unit 105 that carries out labeling of the image data based on the variances, a defect determination unit 106 that determines a type of defect of the web 11 based on a result of labeling carried out by the labeling process part 105, and a defect information recording unit 107 that records defect information acquired based on the defect type determination in a recording medium 108 such as the hard disk.

Note that the defect inspection apparatus 100 and the above-described respective elements are implemented as a result of the inspection personal computer 10 reading and executing the program. The program may be provided by a program providing medium such as a recording medium or a transmission medium. More specifically, for example, the image inputting unit 101 is implemented by a camera interface 10H4 (see FIG. 2), for example.

Also, the density extension and texture correction unit 102, the block division unit 103, the average and variance calculation unit 104, the labeling process unit 105, and the defect determination unit 106 are implemented as a result of the CPU 10H8 (see FIG. 2) executing the program, for example. Further, the defect information recording unit 107 is implemented by the hard disk drive 10H9 (see FIG. 2), for example.

Next, an inspection method for carrying out inspection on the web 11 to determine whether the web 11 has defect by the above-described defect inspection apparatus 100 will be described with reference to FIG. 4.

Figure 4:
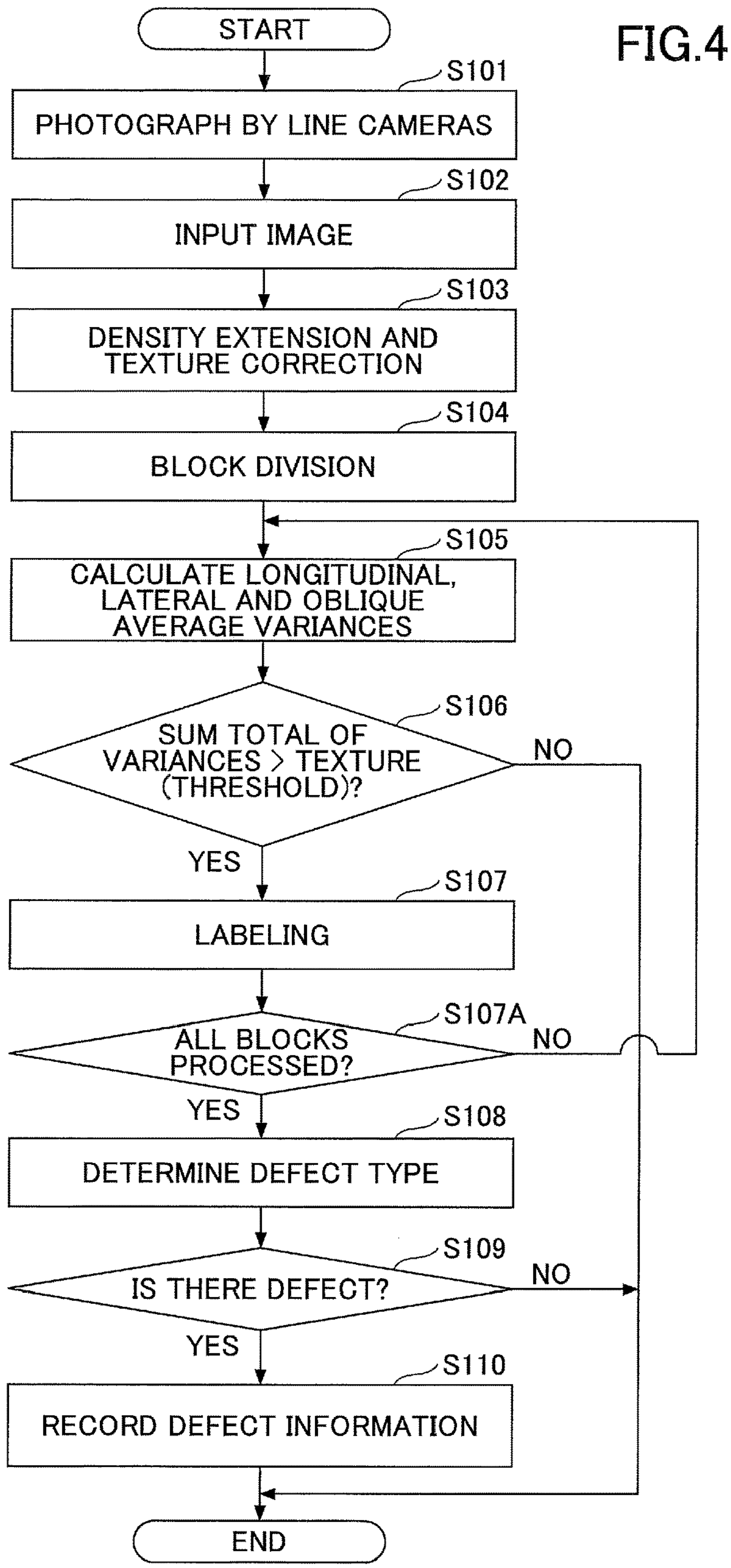
FIG. 4 is a flowchart illustrating a process for inspecting a web to determine whether the web has defect.

FIG. 4 is a flowchart illustrating an inspection procedure for carrying out a process to inspect a web as to whether the web has defect.

First, the defect inspection apparatus 100 irradiates the web 11 conveyed between the conveying rollers 12 with illumination light from the LED 14, and photographs a regularly reflected light image or an irregularly reflected light image of the web 11 in the dark field sensitivity region using the line cameras 13 (step S101).

Image data acquired from the line cameras 13 is converted into digital image data through an analog-to-digital converter, and is input to the image inputting unit 101 of the inspection personal computer 10 (step S102).

The density extension and texture correction unit 102 then carries out density extension correction (i.e., shading correction) on the digital image data (step S103) to correct the brightness of the image.

The process carried out by the density extension and texture correction unit 102 is not limited to the shading correction. The density extension and texture correction unit 102 may carry out another process. For example, the density extension and texture correction unit 102 may carry out at least one of a distortion correction process and a low-pass filtering process, for example. Further, if a color image is used, for example, the density extension and texture correction unit 102 may carry out white balance, for example.

Next, the block division part 103 divides the image represented by the image data on which the shading correction has been carried out into a plurality of blocks each of which has a size of a predetermined number of pixels by a predetermined number of pixels (step S104). The size of each block acquired from the division corresponds to a size in which defect is detected (i.e., a defect detection size).

Figure 5:
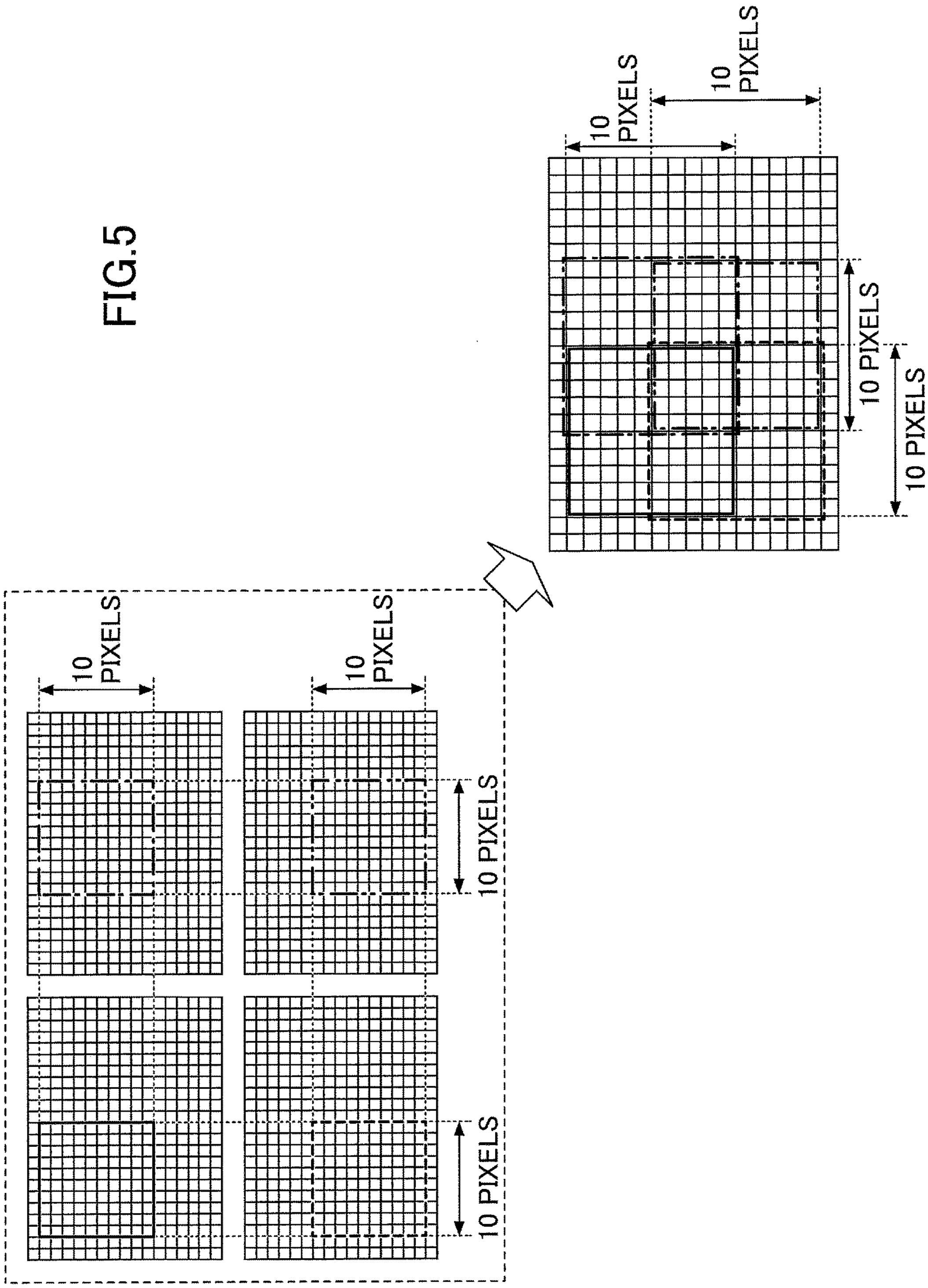
FIG. 5 illustrates one example of a way to divide an image represented by image data into blocks each of which has a size of 10 pixels by 10 pixels, for example, based on a defect detection size.

The division is carried out in such a manner that each block acquired through the division overlaps with other blocks, for example, as illustrated in FIG. 5. Each block size is, for example, 10 pixels by 10 pixels, as illustrated in FIG. 5.

FIG. 5 illustrates one example of a way of dividing the image represented by the image data into blocks each of which has a size of 10 pixels by 10 pixels based on the defect detection size.

Next, the defect inspection apparatus 100 calculates variances of brightness values of the pixels in each of the blocks acquired in step S104 in the longitudinal direction, the lateral direction, and the oblique direction (step S105).

The pixel values used in the calculation are not limited to the brightness values. For example, if a color image is used, the RGB (red-green-blue) values may be used. That is, if the image photographed by the photographing apparatus 13 is acquired as a color image, any of the R values, the G values, the B values, and combinations of the R values, the G values, and the B values may be used.

Which of the R values, the G values, the B values, and combinations of the R values, the G values, and the B values are used can be determined according to the color of the object. For example, if the color of defect is expected as red, the R values may be used from among the R values, the G values, and the B values. Thereby, it is possible to detect defect colored red with high accuracy.

FIG. 6A illustrates an example of calculating the brightness value for each pixel included in the block having the size of 10 pixels by 10 pixels, and calculating directional variances of the blocks.

[Calculation of Lateral Variance]

First, how to calculate a lateral variance in the example illustrated in FIG. 6A will be described.

The "AVERAGE" on the right side in FIG. 6A means the average of the 10 brightness values on each line (in the lateral direction).

The "AVERAGE OF AVERAGES" means the average of the averages of the 10 brightness values on the respective lines 1-10 (each in the lateral direction), and is calculated as 135.7+134.8+132.5+134.2+131.5+128.4+128.8+127.9+129.4+130.1)/10=131.3.

The "SECOND POWER OF AVERAGE" means the second power of the average of the 10 brightness values on each line (in the lateral direction).

The "SUM OF AVERAGES" means the sum of the averages of the 10 brightness values on the respective lines 1-10 (each in the lateral direction).

The "SUM OF SECOND POWERS OF AVERAGES" means the sum of the second powers of the averages of the 10 brightness values on the respective lines 1-10 (each in the lateral direction).

The "LATERAL VARIANCE" means a lateral variance calculated by, for example, subtracting the second power of the "SUM OF AVERAGES" from the "SUM OF SECOND POWERS OF AVERAGES"$\times S_1$, and then, dividing the subtraction result by $(S_1 \times S_2)$, where $S_1$ denotes the lateral block size (the number of pixels), and $S_2$ denotes the longitudinal block size (the number of pixels). In the example illustrated in FIG. 6A, $S_1=S_2=10$.

[Calculation of Longitudinal Variance]

Second, how to calculate a longitudinal variance in the example illustrated in FIG. 6A will be described.

In the same way as that in the case of calculating the lateral variance described above, the "AVERAGE" on the bottom side in FIG. 6A means the average of the 10 brightness values on each column (in the longitudinal direction).

The "AVERAGE OF AVERAGES" means the average of the averages of the 10 brightness values on the respective columns 1-10 (each in the longitudinal direction).

The "SECOND POWER OF AVERAGE" means the second power of the average of the 10 brightness values on each column (in the longitudinal direction).

The "SUM OF AVERAGES" means the sum of the averages of the 10 brightness values on the respective columns 1-10 (each in the longitudinal direction).

The "SUM OF SECOND POWERS OF AVERAGES" means the sum of the second powers of the averages of the 10 brightness values on the respective columns 1-10 (each in the longitudinal direction).

The "LONGITUDINAL VARIANCE" means a longitudinal variance calculated by, for example, subtracting the second power of the "SUM OF AVERAGES" from the "SUM OF SECOND POWERS OF AVERAGES"×$S_2$, and then, dividing the subtraction result by ($S_1$×$S_2$), where $S_1$ denotes the lateral block size (the number of pixels), and $S_2$ denotes the longitudinal block size (the number of pixels).

For example, if the longitudinal variance and the lateral variance are calculated, and the sum of the longitudinal variance and the lateral variance is used as an evaluation value, the evaluation value is calculated as follows, using, for example, the numerals indicated in FIG. 6A.

lateral variance (=7.1311)+longitudinal variance (=9.7311)=evaluation value (=18.8622)

[Calculation of Oblique Variance]

How to calculate an oblique variance will now be described.

Note that when also an oblique (i.e., 45 degrees, for example) variance is calculated on the block of 10 pixels by 10 pixels, the calculation may be made basically in the same way as the way in the case of calculating the lateral variance or the longitudinal variance as described above. However, in this case, the number of pixels used to first calculate the average of the brightness values on each oblique line in the block of 10 pixels by 10 pixels varies depending on the particular oblique line, as illustrated in FIG. 6B.

Figure 6B:
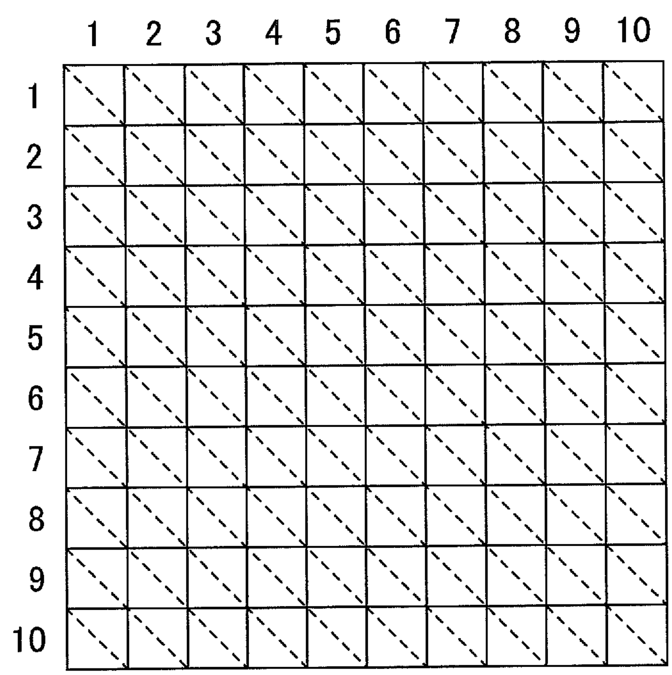

Also, the number of the oblique lines on each of which first the average of the brightness values is calculated is 19, as illustrated in FIG. 6B, in comparison to the case of calculating the longitudinal variance or the lateral variance described above where the number of lines or columns on each of which first the average of the brightness values is calculated is 10.

In FIG. 6B, the broken lines denote the oblique lines of 45 degrees on each of which first the average of the brightness values is calculated. As illustrated in FIG. 6B, the number of the oblique lines is 19 as mentioned above. Also, the number of pixels on each of the 19 oblique lines varies depending on the particular oblique line.

For example, one pixel is on the oblique line at the top right corner in FIG. B. Also, one pixel is on the oblique line at the bottom left corner. In contrast, ten pixels are on the middle oblique line that corresponds to the diagonal line of the block extending between the top left corner and the bottom right corner. Thus the number of pixels on each of the oblique lines 1-19 varies as 1, 2, 3, . . . , 8, 9, 10, 9, 8, . . . , 3, 2, and 1, from the top right corner through the bottom left corner of the block.

Thus, first the average of the brightness values on each oblique line is calculated where the actual number of brightness values on each oblique line varies as 1, 2, 3, . . . , 8, 9, 10, 9, 8, . . . , 3, 2, and 1 corresponding to the above-mentioned variation of the number of pixels, resulting in that the total 19 averages are acquired.

Then, using the thus acquired 19 averages of the brightness values on the respective oblique lines 1-19, the average of the 19 averages is calculated in the same way as the case of calculating the longitudinal variance or the lateral variance.

Also, the second power of the average of the brightness values on each oblique line is calculated, and thereafter, the calculated 19 second powers of the averages of the brightness values on the respective oblique lines are added together to acquire the sum of the second powers of the averages.

Then, the oblique variance is calculated by, for example, subtracting the second power of the sum of the 19 averages of the brightness values from "the sum of the second powers of the averages"×$S_3$, and then, dividing the subtraction result by ($S_3$×$S_3$), where $S_3$ denotes the oblique block size (the number of pixels). In the example illustrated in FIG. 6B, $S_3$=10.

Retuning to FIG. 4, the defect inspection apparatus 100 compares the total sum of the longitudinal variance, the lateral variance and the oblique variance, with a "texture" (i.e., a brightness value threshold) (step S106). If the total sum>texture (i.e., threshold) (YES in step S106), the defect inspection apparatus 100 determines that the corresponding block is a "defect candidate block". Note that the "texture" (i.e., the threshold) is acquired as a variance calculated using the block that has no defect.

In step S107, the defect inspection apparatus 100 labels the defect candidate block determined in step S106. "To label the defect candidate block" means to connect the defect candidate block to another defect candidate block and assign a number to the group of the connected defect candidate blocks.

In step S107A, the defect inspection apparatus 100 determines whether all the blocks acquired in step S104 have been processed. If all the blocks acquired in step S104 have been processed (YES in step S107A), the defect inspection apparatus 100 proceeds to step S108. If all the blocks acquired in step S104 have not been processed yet (NO in step S107A), the defect inspection apparatus 100 returns to step S105 where the defect inspection apparatus 100 calculates the longitude variance, the lateral variance and the oblique variance on the next block.

The defect inspection apparatus 100 then determines whether the web has defect and determines a type of the defect (hereinafter, simply referred to as a "defect type") (step S108).

That is, the defect inspection apparatus 100 compares the longitudinal length, the lateral length, and the area of the group of labeled (connected) defect candidate blocks with predetermined thresholds, respectively. If any one of the longitudinal length, the lateral length, and the area of the group of labeled defect candidate blocks is longer or larger than or equal to the corresponding threshold, the defect inspection apparatus 100 determines that the web has defect (YES in step S109).

If none of the longitudinal length, the lateral length, and the area is longer or larger than or equal to the corresponding threshold, the defect inspection apparatus 100 determine that the web has no defect (NO in step S109).

In more detail, the defect inspection apparatus 100 determines that a group of labeled defect candidate blocks corresponds to defect of a longitudinal stripe if the group of labeled defect candidate blocks extends longitudinally to have a longitudinal length longer than or equal to a predetermined longitudinal threshold.

In the same way, the defect inspection apparatus 100 determines that a group of labeled defect candidate blocks corresponds to defect of a lateral stripe if the group of labeled defect candidate blocks extends laterally to have the lateral length longer than or equal to a predetermined lateral threshold.

The defect inspection apparatus 100 determines that a group of labeled defect candidate blocks corresponds to defect of unevenness if the group of labeled defect candidate blocks extends longitudinally and laterally to have the area larger than or equal to a predetermined area threshold.

Figure 7:
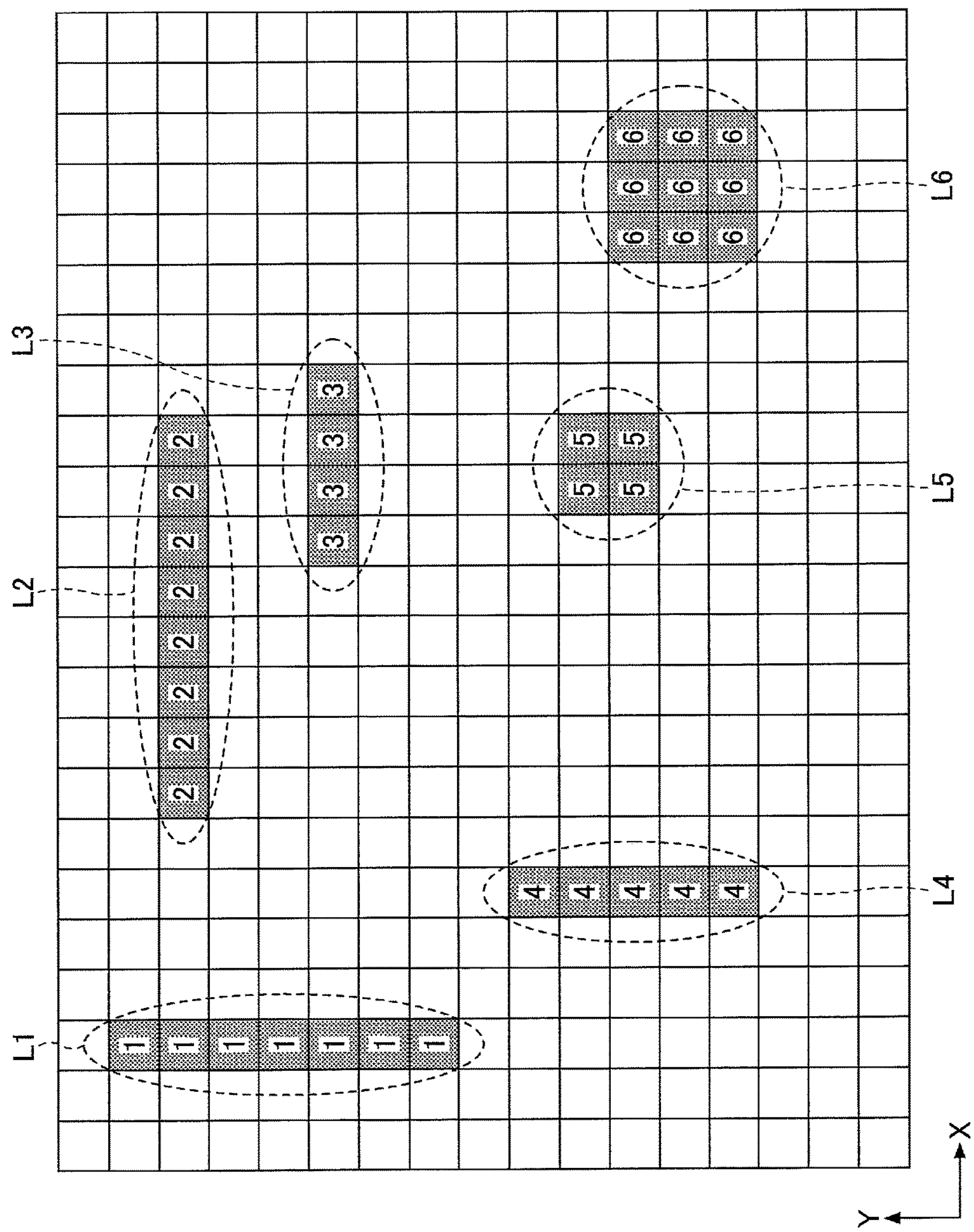
FIG. 7 illustrates one example of a determination result.

FIG. 7 illustrates examples of determination results of step S109. In FIG. 7, each square corresponds to the block. Below, an "X direction" denotes the lateral direction, and a "Y direction" denotes the longitudinal direction.

If a group of labeled defect candidate blocks includes six or more blocks connected in the X direction, the defect inspection apparatus determines that the group of labeled defect candidate blocks as defect of a “lateral stripe”.

If a group of labeled defect candidate blocks includes six or more blocks connected in the Y direction, the defect inspection apparatus determines that the group of labeled defect candidate blocks as defect of a “longitudinal stripe”.

If a group of labeled defect candidate blocks includes nine or more blocks connected in the X direction and the Y direction, the defect inspection apparatus determines that the group of labeled defect candidate blocks as defect of “unevenness”.

Below, an example of determination results acquired using these determination criteria will be described.

In FIG. 7, the colored pixels (i.e., gray pixels in FIG. 7) denote the defect candidate blocks determined in step S106 in FIG. 4. Further, the numerals written in the blocks denote label numbers given by the labeling in step S107 in FIG. 4.

The group of defect candidate blocks having the label number “1” (hereinafter, referred to as a “first label group L1”) includes 7 defect candidate blocks successively occurring in the Y direction, and thus the length of the group in the Y direction is longer than or equal to the longitudinal threshold (i.e., 6). Therefore, the first label group L1 is determined as defect of a “longitudinal stripe”.

The group of defect candidate blocks having the label number “2” (hereinafter, referred to as a “second label group L2”) includes 8 defect candidate blocks successively occurring in the X direction, and thus the length of the group in the X direction is longer than or equal to the lateral threshold (i.e., 6). Therefore, the second label group L2 is determined as defect of a “lateral stripe”.

The group of defect candidate blocks having the label number “3” (hereinafter, referred to as a “third label group L3”) includes 4 defect candidate blocks successively occurring in the X direction, and thus the length of the group in the X direction is shorter than the lateral threshold (i.e., 6). Therefore, the third label group L3 is not determined as defect of a “lateral stripe”.

The group of defect candidate blocks having the label number “4” (hereinafter, referred to as a “fourth label group L4”) includes 5 defect candidate blocks successively occurring in the Y direction, and thus the length of the group in the X direction is shorter than the longitudinal threshold (i.e., 6). Therefore, the fourth label group L4 is not determined as defect of a “lateral stripe”.

The group of defect candidate blocks having the label number “5” (hereinafter, referred to as a “fifth label group L5”) includes 4 defect candidate blocks adjacently occurring in the X direction and the Y direction, and thus the area of the group is smaller than the area threshold (i.e., 9). Therefore, the fifth label group L5 is not determined as defect of “unevenness”.

The group of defect candidate blocks having the label number “6” (hereinafter, referred to as a “sixth label group L6”) includes 9 defect candidate blocks adjacently occurring in the X direction and the Y direction, and thus the area of the group is larger than or equal to the area threshold (i.e., 9). Therefore, the sixth label group L6 is determined as defect of “unevenness”.

Thus, determines whether a web has defect based on a length and an area of a group of labeled defect candidate blocks, i.e., a length and an area in which the blocks determined as exceeding “texture” are connected. Also, the defect inspection apparatus 100 determines a type of the defect such as defect of a “lateral stripe”, defect of a “longitudinal stripe”, or defect of “unevenness”. The determination criteria (thresholds) are previously set through an operation of a user, for example, in the defect inspection apparatus 100.

If the defect inspection apparatus 100 determines in step S109 that the web has defect (YES in step S109), the defect inspection apparatus records, in a recording medium 108 (see FIG. 3) such as the hard disk, information such as information of the defect image, the corresponding position information, the type of defect, and the size of defect (step S110), and ends the process.

If the defect inspection apparatus 100 determines in step S106 that the total sum of the variance values is less than or equal to the texture (i.e., the threshold) (NO in step S106), the defect inspection apparatus 100 determines that the blocks, i.e., the web, have no defect, and ends the process.

According to the embodiment, the defect determination conditions include the condition concerning the sum of the longitudinal variance, the lateral variance, and the oblique variance. Thus, the defect detection sensitivity is improved, and “light unevenness” can be detected. “Light unevenness” means a sort of unevenness that lies in a wide area such that a brightness difference between adjacent pixels is less than brightness differences in other sorts of defect, and the brightness difference gradually increases in the area. The “light unevenness” is also called “firefly defect” concerning printed matter defect.

FIG. 8 illustrates a comparison between a calculation speed (1/(line rate)) to inspect a web to determine whether the web has defect using “directional variances”, i.e., the longitudinal variance and the lateral variance of brightness, described above, and process speeds for one line using an averaging filter and a median filter. That is, FIG. 8 compares, based on the specification (8192 pixels) of the camera, processing speeds for a case of processing one line that includes 8192 pixels in the main scanning direction.

Figure 9:
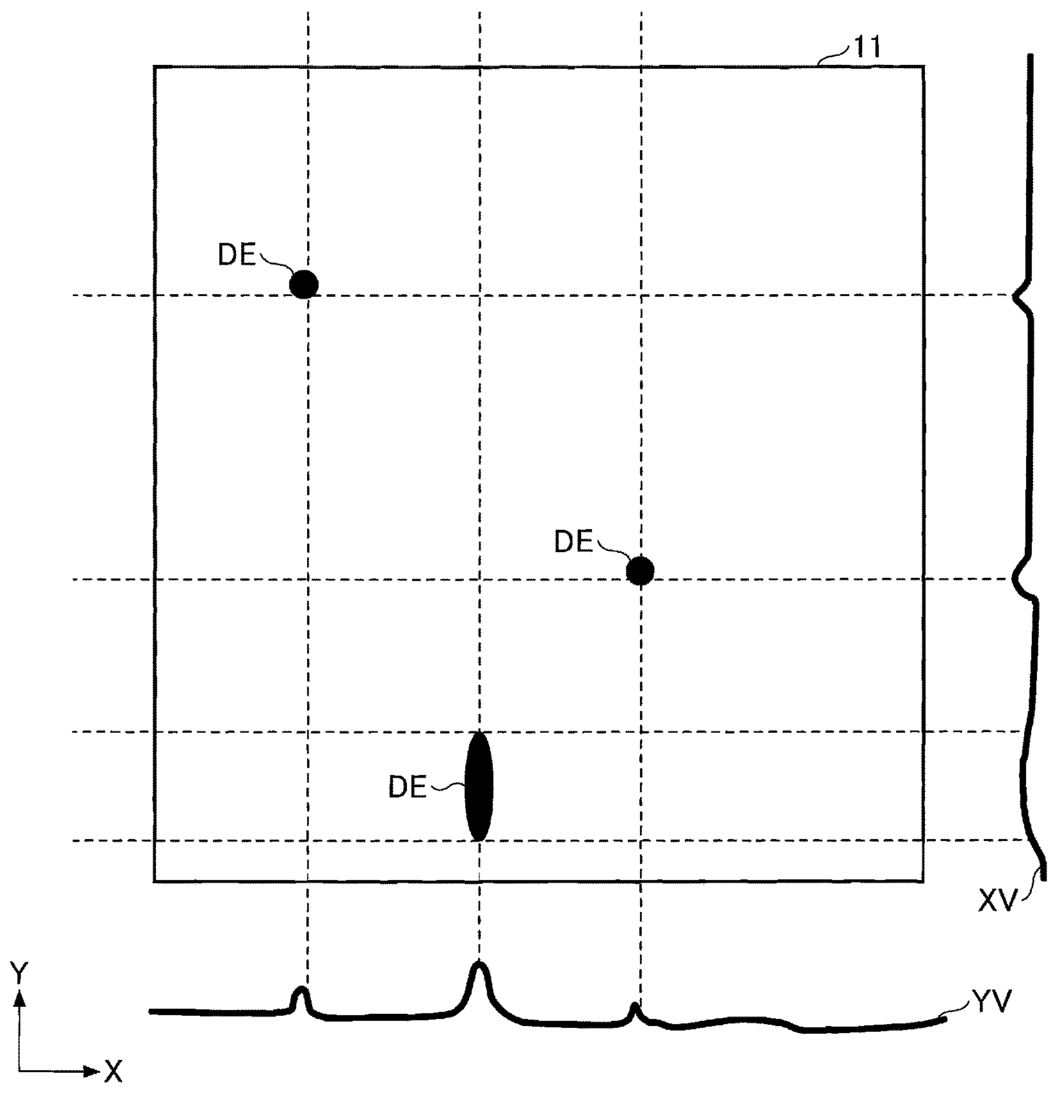
FIG. 9 illustrates one example of cumulative values for calculating directional variances.

FIG. 9 illustrates one example of a cumulative value for calculating directional variances. For example, by using the directional variances, defect DE can be detected in the following way. Below, description will be made for a case where the web 11 has defect DE as illustrated in FIG. 9.

First, as illustrated in FIG. 9, the defect inspection apparatus 100 calculates the variance in the X direction (hereinafter, referred to as an “X-direction variance XV”), and the variance in the Y direction (hereinafter, referred to as a “Y-direction variance YV”). Thereby, as illustrated in FIG. 9, if there is defect DE, the X-direction variance XV and the Y-direction variance YV are increased at the corresponding point than the X-direction variance XV and the Y-direction variance YV at the other points. Therefore, it is possible to detect the defect DE based on the X-direction variance XV and the Y-direction variance YV.

The line rate (1/(number of lines (i.e., 2048 in the sub-scanning direction))/(time required for a filtering process) means, in the same manner as a scan rate (1/(number of lines (i.e., 2048 in the sub-scanning direction))/(time required for a scanning process) expressed for a line camera, a time required for processing one line, expressed as a frequency. Therefore, the higher the line rate is, the higher the processing speed is.

The method according to the embodiment of the present invention using the directional variances will now be compared with a method in the related art using an averaging filter.

Although the filter sizes (i.e., the kernel sizes) are different, lengths (i.e., 31 pixels and 40 pixels) in which defect of a stripe can be detected are equivalent between the method using an averaging filter of 1×31 and the method using directional variances of 40×40.

However, in comparison to the line rate that is 888.43 in the method using directional variances of 40×40, the line rate is 314.96 in the method using the averaging filter. Thus, it can be seen that the processing speed in the method using directional variances is higher in the ratio of 888.43/314.96, i.e., about 2.8 times the processing speed in the method using the averaging filter.

The reason why the processing speed of the method using directional variances according to the embodiment of the present invention is higher than the method using an averaging filter and the method using a median filter that are commonly used is that the required number of writing in a memory is smaller although the calculation costs are higher according to the embodiment of the present invention.

That is, for example, if an averaging filter is used, an average is written in a memory for each pixel of a block. In contrast thereto, according to the embodiment of the present invention using directional variances, a variance is written in a memory merely for each block.

Specifically, the number of times of writing in a memory will now be calculated assuming that the main scanning block size is 20 pixels, the sub-scanning block size is 20 pixels, and the number of pixels of a line camera is 8192.

According to the method using an averaging filter, the number of times of writing in a memory is calculated as 8192×2048=16,777,216 (times). In contrast thereto, according to the embodiment of the present invention using directional variances, the number of times of writing in a memory is calculated as (8192/20)×2×(2048/2)×2=1,677,722 (times).

Thus, by using the algorithm according to the embodiment of the present invention described above, it is possible to reduce the number of times of writing in a memory by about 1/10 in comparison to the case of using an averaging filter.

As described above, according to the defect inspection apparatus of the embodiment of the present invention, image data is divided into blocks each of which has a predetermined size, and a web is inspected using directional variances acquired for each block. Therefore, in comparison to the related art, it is possible to carry out inspection at high speed. Also, it is possible to implement the method according to the embodiment of the present invention, using a single algorithm for detecting defect. Therefore, it is possible to reduce the size of algorithm (i.e., increase the speed of inspecting defect).

Note that, the number of pixels as the dimension of the block according to the embodiment of the present invention is previously determined. For example, the number of pixels may be determined depending on the specification of the line camera, i.e., the number of pixels of a photo sensor that the line camera has.

Also, the number of pixels as the dimension of the block according to the embodiment of the present invention may be determined depending on an object to inspect. For example, if a size or a length of defect to be detected can be estimated, the number of pixels may be determined based on resolution at which defect can be detected.

It is also possible to previously select pixels to be processed from among pixels for which the photo sensor of the line sensor outputs as image data. If pixels to be processed are limited, a processing load of a subsequent stage can be reduced.

According to the embodiment of the present invention, it is possible to reduce a defect inspection processing time, and achieve improvement in a defect inspection speed in a defect inspection apparatus for inspecting a sheet-like inspection object.

Thus, the defect inspection apparatuses for inspecting sheet-like inspection object, computer-implemented methods for inspecting sheet-like inspection object, and defect inspection systems for inspecting a sheet-like inspection object have been described in the embodiments. However, embodiments are not limited to the above-described embodiments, and various modifications and replacements may be made.

What is claimed is:

1. A defect inspection apparatus for inspecting a sheet-like inspection object using a photographed image of the sheet-like inspection object, the photographed image being input from a photographing apparatus, the defect inspection apparatus comprising:

at least one processor configured to divide the photographed image of the sheet-like inspection object into blocks each of which has a size of a first predetermined number of pixels by a second predetermined number of pixels;

calculate, for each block, a longitudinal variance based on pixel values in a longitudinal direction in the block and a lateral variance based on pixel values in a lateral direction in the block;

determine, for each block, whether the block is a defect candidate using the longitudinal variance and the lateral variance as sheet-like inspection object defect determination evaluation values; and determine that the sheet-like inspection object has a first type of defect based on a first number of consecutive blocks in the photographed image determined as the defect candidates exceeding a length threshold, and that the sheet-like inspection object has a second type of defect based on a second number of consecutive blocks in the photographed image determined as the defect candidates exceeding an area threshold, wherein the first type of defect corresponds to a stripe defect and the second type of defect corresponds to an unevenness defect.

2. The defect inspection apparatus according to claim 1, wherein the at least one processor is further configured to further calculate an oblique variance based on pixel values in an oblique direction in each block; and determine whether the block is a defect candidate further using the oblique variance as another sheet-like inspection object defect determination evaluation value.

3. The defect inspection apparatus according to claim 1, wherein the at least one processor is further configured to determine that the block is a defect candidate if a total sum of variances acquired by calculating is higher than or equal to a threshold.

4. The defect inspection apparatus according to claim 2, wherein the at least one processor is further configured to determine that the block is a defect candidate if a total sum of variances acquired by calculating is higher than or equal to a threshold.

5. The defect inspection apparatus according to claim 3, wherein the at least one processor is further configured to label the blocks determined as the defect candidates.

6. The defect inspection apparatus according to claim 4, wherein the at least one processor is further configured to label the blocks determined as the defect candidates.

7. The defect inspection apparatus according to claim 1, wherein the photographed image is a color image, and wherein each pixel value is at least one of a brightness value and a RGB value.

8. The defect inspection apparatus according to claim 2, wherein the photographed image is a color image, and wherein each pixel value is at least one of a brightness value and a RGB value.

9. The defect inspection apparatus according to claim 3, wherein the photographed image is a color image, and wherein each pixel value is at least one of a brightness value and a RGB value.

10. The defect inspection apparatus according to claim 4, wherein the photographed image is a color image, and wherein each pixel value is at least one of a brightness value and a RGB value.

11. The defect inspection apparatus according to claim 5, wherein the photographed image is a color image, and wherein each pixel value is at least one of a brightness value and a RGB value.

12. The defect inspection apparatus according to claim 6, wherein the photographed image is a color image, and wherein each pixel value is at least one of a brightness value and a RGB value.

13. A computer-implemented method for inspecting a sheet-like inspection object using a photographed image of the sheet-like inspection object, the photographed image being input from a photographing apparatus, the method comprising:

dividing, with at least one processor, the photographed image of the sheet-like inspection object into blocks each of which has a size of a first predetermined number of pixels by a second predetermined number of pixels;

calculating, by at least one processor for each block, a longitudinal variance based on pixel values in a longitudinal direction in the block and a lateral variance based on pixel values in a lateral direction in the block;

determining, with at least one processor for each block, whether the block is a defect candidate using the longitudinal variance and the lateral variance as sheet-like inspection object defect determination evaluation values;

determining, with at least one processor, that the sheet-like inspection object has a first type of defect based on a first number of consecutive blocks in the photographed image determined as the defect candidates exceeding a length threshold; and determining, with at least one processor, that the sheet-like inspection object has a second type of defect based on a second number of consecutive blocks in the photographed image determined as the defect candidates exceeding an area threshold, wherein the first type of defect corresponds to a stripe defect and the second type of defect corresponds to an unevenness defect.

14. The computer-implemented method according to claim 13, further comprising:

further calculating, with at least one processor, an oblique variance based on pixel values in an oblique direction in each block; and determining, with at least one processor, whether the block is a defect candidate further using the oblique variance as another sheet-like inspection object defect determination evaluation value.

15. The computer-implemented method according to claim 13, further comprising:

labeling, with at least one processor, the blocks determined as the defect candidates.

16. The computer-implemented method according to claim 14, further comprising:

labeling, with at least one processor, the blocks determined as the defect candidates.

17. A defect inspection system for inspecting a sheet-like inspection object, the defect inspection system comprising:

a photographing apparatus; and at least one processor configured to divide a photographed image of a sheet-like inspection object into blocks each of which has a size of a first predetermined number of pixels by a second predetermined number of pixels, the photographed image being input from the photographing apparatus;

calculate, for each block, a longitudinal variance based on pixel values in a longitudinal direction in the block and a lateral variance based on pixel values in a lateral direction in the block;

determine, for each block, whether the block is a defect candidate using the longitudinal variance and the lateral variance as sheet-like inspection object defect determination evaluation values;

determine that the sheet-like inspection object has a first type of defect based on a first number of consecutive blocks in the photographed image determined as the defect candidates exceeding a length threshold; and determine that the sheet-like inspection object has a second type of defect based on a second number of consecutive blocks in the photographed image determined as the defect candidates exceeding an area threshold, wherein the first type of defect corresponds to a stripe defect and the second type of defect corresponds to an unevenness defect.

* * * * *